United States Patent
Kendig et al.

(10) Patent No.: US 8,211,283 B2
(45) Date of Patent: Jul. 3, 2012

(54) MICROFABRICATED LIQUID JUNCTION REFERENCE ELECTRODE

(75) Inventors: Martin W. Kendig, Thousand Oaks, CA (US); Jeffrey F. DeNatale, Thousand Oaks, CA (US)

(73) Assignee: Teledyne Scientific & Imaging, LLC, Thousand Oaks, CA (US)

( * ) Notice: Subject to any disclaimer, the term of this patent is extended or adjusted under 35 U.S.C. 154(b) by 441 days.

(21) Appl. No.: 12/555,681

(22) Filed: Sep. 8, 2009

(65) Prior Publication Data
US 2011/0056831 A1    Mar. 10, 2011

(51) Int. Cl.
*G01N 27/30* (2006.01)
(52) U.S. Cl. ....................................... 204/435
(58) Field of Classification Search .............. 204/435
See application file for complete search history.

(56) References Cited

U.S. PATENT DOCUMENTS
2008/0000771 A1 *   1/2008   Kakiuchi et al. .............. 204/435

FOREIGN PATENT DOCUMENTS
WO     WO 2010021536 A2 *   2/2010
* cited by examiner

*Primary Examiner* — Alex Noguerola
(74) *Attorney, Agent, or Firm* — Glenn H. Lenzen; Husch Blackwell LLP

(57) ABSTRACT

A microfabricated liquid junction reference electrode that can be integrated with microfabricated chemical or electrical sensors, which electrode is an M/MX type reference electrode comprised of a metal and a metal salt, as well as a $X^-$ Containing Ionic Liquid having a constant activity of $X^-$ and a porous thin-film membrane impregnated with a Hydrophobic Ionic Liquid.

20 Claims, 2 Drawing Sheets

US 8,211,283 B2

MICROFABRICATED LIQUID JUNCTION REFERENCE ELECTRODE

FIELD OF THE INVENTION

The present invention relates to a microfabricated liquid junction reference electrode containing an immobilized Hydrophobic Ionic Liquid for integration with microfabricated chemical and electrical sensors. In particular, the reference electrode is comprised of a metal electrode of metal M covered by a reversibly formed oxidation product layer immersed in an immiscible Ionic Liquid containing an anion reactant, the ionic liquid being separated from an aqueous analyte by a porous membrane containing a protective Hydrophobic Ionic Liquid.

BACKGROUND

Electrochemical sensors are used to determine the concentrations of various analytes in testing samples such as fluids and dissolved solid materials. A typical electrochemical sensor consists of three electrodes: a sensing electrode, a counter electrode, and a reference electrode. The accuracy of a particular sensor's measurements depends on the ability to measure the potential difference between the sensing electrode, whose potential varies with the analyte concentration in the measured sample analyte solution, and the reference electrode, which ideally maintains constant potential.

In typical, commercially available electroanalytical measurement systems, the physical interface between the reference electrode (typically the electrolyte of the reference electrode) and the sample solution is referred to as the liquid junction. The potential at the metal electrode within the liquid of the liquid junction is related to a number of factors; it is an object of every reference electrode design to minimize the effect of the factors that would cause the potential of the electrode to vary in any way over time. However, the liquid junction and the potential between the metal electrode and the outside environment are difficult to control and maintain at a constant level. Typically, it is the change in the electrode potential of the metal within the liquid junction that introduces error into the electrochemical measurement and causes the need for frequent sensor calibration.

One problem with junction structures is that they typically allow the sample analyte solution to enter the junction structure, which limits the useful lifetime of the reference electrode. This transport of analyte solution into the junction, whether by diffusion, migration, convection, or other means, results in the contamination of the junction structure and a resultant undesirable variation in the liquid junction potential. Such variation typically necessitates recalibration of the electroanalytical measurement system. If this type of contamination continues over time, the junction structure may become fouled or clogged and develop even larger offset potentials and/or potentials that chronically drift despite repeated attempts at recalibration. Such contamination takes away from the robustness of a reference electrode and prevents it from being used for long periods of time (i.e., long-lived). In addition, the analyte solution will often transport past the junction structure and reach the reference half-cell, possibly causing additional adverse reactions.

Another problem associated with the junction relates to the requirement that the activity of an ion or several ions or compounds in the electrolyte adjacent to the reference electrode must remain constant. The activity of such species must remain constant since they equilibrate with the electrode so as to fix the absolute potential at a constant value.

Accordingly, the stability of the reference electrode and hence, the accuracy of the potentiometric measurements, are dependent on the constancy of the liquid junction, the constancy of the ionic activity of an ion or compound that determines the potential of the electrode, and the constancy of the potential across the ionic liquid. If a highly stable and reliable reference electrode is not used for electrochemical measurements, the deviation in the potential leads directly to a measurement error. As such, the reference electrode is a basic and important element for the electrochemical sensor.

The use of reference electrodes is typically necessary in the field of microelectromechanical systems (MEMS). One subset of MEMS devices are Lab-on-a-Chip devices (LOCs), which are devices that integrate one or several laboratory functions on a single chip of only millimeters to a few square centimeters in size. LOCs deal with the handling of extremely small fluid volumes down to less than pico liters. While considerable development has been directed toward producing electrochemical microsensors, such as ion specific or enzyme specific electrodes, little progress has been made in the development of a suitably robust microfabricated reference electrode for use with MEMS or LOC devices. The unavailability of a microfabricated liquid junction reference electrode that is both stable and long-lived has restricted the use of microelectrochemical sensors in industrial and biomedical applications. Heretofore, researchers have used chloridized silver wire as the (pseudo) reference electrode, upon considering the analyte pH and chloride ion concentrations to be relatively constant. However, use of chloridized silver wire renders the sensors non-robust and subject to fouling and failure or unexpected chemistries that change the activity of the potential-controlling compound or ion. In many cases, macroscopic double liquid junction reference electrodes have been used in the absence of a reliable microfabricated reference electrode. However, use of a macroscopic reference electrode makes the sensor as a system large and complex. Therefore, a need exists for an improved microfabricated liquid junction reference electrode.

Accordingly, there is still a need in the art for a nominally co-planar, micro-fabricated liquid junction reference electrode that is highly stable and reliable, robust, and which can be integrated to microfabricated chemical sensors and MEMS devices.

SUMMARY OF THE INVENTION

The present invention is directed towards a microfabricated liquid junction reference electrode that can be integrated with microfabricated chemical or electrochemical sensors to measure conductivity of an aqueous analyte. The present invention also includes a method of making the reference electrode.

The reference electrode of the present invention is a "M/MX" electrode, such as a silver/silver chloride electrode, and is held in contact with a support substrate. The support substrate is comprised of an electrically conducting material. The electrode is separated from an aqueous analyte by an ionic liquid. The ionic liquid is immiscible and maintains a constant activity of the potential-controlling compound or ion. The electrode is further separated from the aqueous analyte by a porous thin-film membrane. The thin-film membrane is filled with an immobilized but ionically conducting hydrophobic ionic liquid.

The method of making the reference electrode generally includes depositing a first layer comprised of a conductive noble metal onto a non-conducting structure, which is connected to a conducting support substrate. After the conductive metal has been deposited, a M/MX type reference electrode is formed by annealing the conductive metal in a halide to produce a metal salt layer on top of the conductive noble metal layer. The electrode is then covered with an ionic liquid having a constant absolute activity of $X^-$, the potential-controlling ion. The conducting support substrate is isolated from the analyte by an insulator. Finally, a porous thin-film membrane is filled with a hydrophobic ionic liquid and is placed over the ionic liquid-filled electrode. The presence of ionic liquid phases ensures that the reference electrode maintains a constant absolute potential, as governed by the constant activity of $X^-$, and the exclusion of other ions or compounds that would influence the potential of the electrode compose of M and covered by the layer MX.

Alternatively, either the ionic liquid that maintains the constant X-activity and the hydrophobic membrane may be formed by partial cross-linking of the liquid or through the addition of an appropriate gellant (such as polyvinylidene hexa fluoroproplyene [Mantz, Sutto, DeLong and Truelove, Z. Naturforsch. 57 a, 839-846 (2002), Cyclo(L-α-3,7-dimethylctylasparaginyl-L-phenylalanyl), and Cyclo(L-α-2-ethylhexylasparaginyl-L-phenylaianyl) [Hanabusa et al., Langmuir 2005, 21, 10383-10390]).

The reference electrode of the present invention provides advantages over reference electrodes in the prior art, since the use of ionic liquid phases makes the electrode both stable and long lasting. Maintaining a constant absolute potential within the device through the use of ionic liquid phases makes the reference electrode stable when used with chemical sensors to analyze an aqueous analyte. Additionally, the inclusion of the porous membrane containing a Hydrophobic Ionic Liquid enables the electrode to be long lasting, due to the fact that the membrane serves to prevent the aqueous analyte from fouling the junction and/or reaching the conducting support substrate.

DETAILED DESCRIPTION OF THE INVENTION

Figure 1:
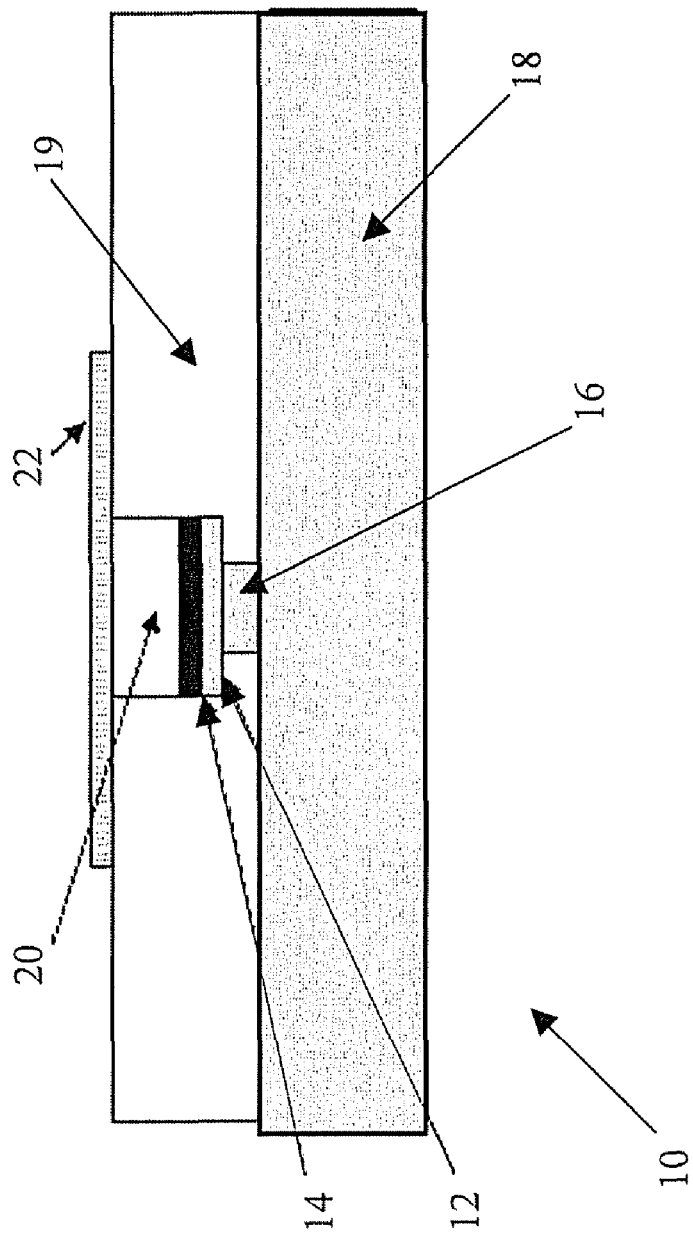
FIG. 1 is a cross-sectional view of the microfabricated electrochemical sensor containing the reference electrode.
Figure 2:
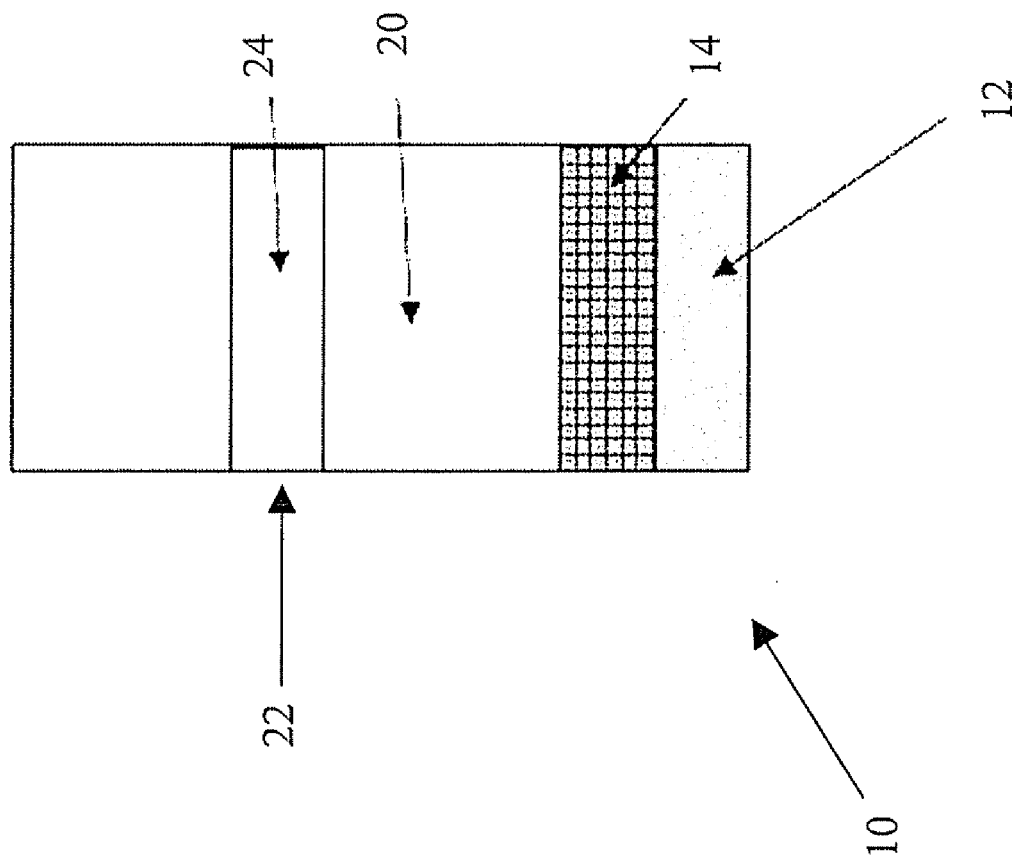
FIG. 2 is an exploded view of a portion of the reference electrode.

In accordance with the present invention, a reference electrode as shown in FIGS. 1 and 2 and method of making a reference electrode have been developed. The present invention provides a microfabricated reference electrode for use with microfabricated chemical or electrical sensors to measure characteristics of fluid or liquid samples. The microfabricated liquid junction reference electrode of the present invention uses hydrophobic and immiscible ionic liquids to form the junction and maintain a constant activity of the electrochemical reagent. As such, the reference electrode of the present invention can perform for relatively long periods of time, is robust and provides a substantially constant potential that is substantially free of errors as compared to other microfabricated reference electrodes known in the prior art.

As illustrated in FIGS. 1 and 2, the reference electrode 10 of the present invention is generally planar-shaped and is preferably an M/MX type electrode, wherein M is a noble metal and MX is a metal salt. The reference electrode 10 is comprised of a metal layer 12, which consists of a noble metal. In a preferred embodiment, the metal layer 12 is silver. Alternatively, the noble metal used for the metal layer 12 may be any of a variety of metals such as platinum, gold, silver, copper, nickel, rhodium, palladium, ruthenium, osmium, iridium, or combinations thereof. The noble metal 12 may be deposited onto a conducting structure 16 preferably having a depth of in the range of 1 μm to 2.0 mm. The conducting structure 16 is connected to a conducting support substrate 18 or backplane as shown in FIG. 1. Materials used for the conducting substrate 18 consist mainly of conductive materials such as, for example, aluminum, noble metals, or combinations thereof, enabling electronic contact to transduction circuitry. The conducting substrate 18 allows the reference electrode 10 to connect to a potentiometric device or system. The conducting substrate 18 must be isolated from the aqueous analyte with a sealing insulator 19. The materials having excellent properties of water-resistance, heat-resistance, chemical-resistance and close adherence to an electrode are preferable. In a preferred embodiment, the potential of the electrode 10 is constant over as broad a range as possible in pH and an ionic concentration of between $1^{-9}$ and 1 Molar (Mol/L).

A metal salt layer 14 is formed over the metal layer 12 of the reference electrode 10. The metal salt layer 14 consists of a metal salt of anion $X^-$. To form the metal salt layer 14, the metal layer 12 is treated with a reagent providing an oxidant and an active form of $X^-$. The intensity of the treatment and, thus, the thickness of the formed metal salt layer 14, can be adjusted by the conditions of the treatment such as exposure time, concentration of the reagents, and temperature. Suitable treatment conditions can vary depending on, for example, the specific noble metal used and the desired thickness of the metal salt layer 14. In a preferred embodiment, the silver metal layer 12 is treated with chlorine gas at an elevated temperature and a silver chloride layer 14 is formed over the silver metal layer 12 of the electrode 10. In alternative embodiments, the metal salt layer 14 may be formed by anodizing the metal layer 12 in an KCl solution, immersing the metal layer 12 in an HCl solution, immersing the metal electrode in a bleach solution, or exposing the metal layer 12 to a reactive chlorine-containing plasma.

The metal layer 12 and the metal salt layer 14 are further in contact with a $X^-$ Containing Ionic Liquid 20 opposite the metal layer 12. The $X^-$ Containing Ionic Liquid 20 maintains a constant activity of $X^-$, which in turn, enables the electrode 10 to maintain a constant absolute potential. Preferably, the $X^-$ Containing Ionic Liquid 20 is immiscible with water and/or with other ionic liquids, and is immobilized through gelation or partial polymerization or as a neat high viscosity ionic liquid. In a preferred embodiment, a di-alkyl imidazolium chloride is gelled as described by Sufto et al. (Z. Naturforsch., 57a, 839 (2002)) using poly-vinylidene difluoride hexafluoropropylene, but with the gel applied to the electrode 10 when still in the liquid state and then allowed to set or cure under flowing nitrogen as described in the reference.

The reference electrode 10 is further separated from an aqueous analyte by a thin-film membrane 22. The thin-film membrane 22 immobilizes the $X^-$ Containing Ionic Liquid 20 over the metal salt layer 14. The thin-film membrane 22 is any sufficient width and length to adequately contain the $X^-$ Containing Ionic Liquid 20. Preferably, the thickness of the thin-film membrane 22 is less than 1 μm.

The thin-film membrane 22 may be any micro porous or nano porous material, organic or inorganic polymer, gel matrix, or insulating metal oxide that has a continuous network of pores enabling ionic percolation by an electrolyte. The layers making up the thin-film membrane 22 may be made from porous cellulose with nano pores or micro pores generated by particle irradiation, or the layers may be made by the sol gel process, selected phase extraction from a two phase polymer, partial polymerization of an ionic liquid, partial photo-polymerization of an ionic liquid, or a combination thereof. Additionally, the thin-film membrane 22 may be made from a non-conducting solid that contains an immobilized network (above the percolation threshold) of ionically conducting material having constant reactant activity. Preferably, the thin film membrane 22 is comprised of polyethylene oxide or a polyethylene glycol gel, as described in detail in Fabrication and Characterization of a New Planar Solid-State Reference Electrode for ISFET Sensors, Thin Solid Films, vol. 406(1-2), pp. 255-261, Huang et al. (2002). A variety of materials may be used for the thin-film membrane 22, provided the material is ionically conducting, not electronically conducting, and hydrophobic to resist water penetration or dissolution by water. The thin-film membrane 22 may have any thickness, however, it is preferable that the thin-film membrane 22 be as thin as possible, preferably less than or equal to 1 micron. In alternative embodiments, the thin-film membrane 22 has a thickness of 0.1 μm-10 μm, 0.1 μm-5.0 μm, or 0.5 μm-1.0 μm.

The size of the pores 24 in the thin-film membrane 22 preferably ranges from 10 nm-10 μm. The thin-film membrane 22 is further preferably comprised of a Hydrophobic Ionic Liquid. The concentration of the Hydrophobic Ionic Liquid in the thin-film membrane 22 is preferably at least 30% by volume. The Hydrophobic Ionic Liquid filled thin-film membrane 22 prevents loss of the $X^-$ Containing Ionic Liquid 20 into the test environment, as well as influx of the aqueous analyte into the reference electrode 10. Prevention of this back diffusion and influx of liquid contributes to the junction potential remaining stable and free of errors, and constant activity of the $X^-$ anion over a period of a year or more.

In a preferred embodiment of the present invention, the reference electrode 10 is a double junction electrode comprised of the thin-film membrane 22 impregnated with a Hydrophobic Ionic Liquid. In alternative embodiments of the present invention, the reference electrode 10 is a single junction electrode wherein the thin-film membrane 22 is not used and instead, the $X^-$ Containing Ionic liquid 20 is also hydrophobic and contains a constant activity for the anion, $X^-$.

A method for making the reference electrode 10 is also disclosed. The method for making the electrode 10 includes depositing a conductive noble metal onto a conducting structure 16 that is connected to a conducting support substrate 18, thereby forming the metal layer 12 of the electrode 10. A metal salt layer 14 is formed above the metal layer 12 by treating the metal layer 12 with a reagent providing an oxidant and an active form of $X^-$ to produce the metal salt layer 14. The electrode 10 is covered with a $X^-$ Containing Ionic Liquid 20 having a constant activity of $X^-$. A porous thin-film membrane 22 containing a Hydrophobic Ionic Liquid is placed over the electrode 10 and separates the $X^-$ Containing Ionic Liquid 20 and the reference electrode 10 from the aqueous analyte. The conducting support substrate 18 is further isolated from the aqueous analyte by an insulator 19.

DEFINITIONS

Unless otherwise defined, all technical and scientific terms used herein have the same meaning as commonly understood by one of ordinary skill in the art to which this invention belongs. To facilitate understanding of the invention, several terms are defined below.

The term "aqueous analyte" refers to any fluid or solution which may be tested using the reference electrode, including, for example, an aqueous solution, such as a reference or calibrating solution, or a body fluid, such as blood, plasma, synovial fluid, and urine.

The term "$X^-$ Containing Ionic Liquid" refers to an ionic liquid or combination of ionic liquids selected from but not limited to the following: 1-butyl-3-methylimidazolium chloride; 1-n-butyl-3-methylimidazolium chloride, 1-Butyl-2,3-dimethylimidazolium chloride, 1-Butyl-1-methylpyrrolidinium chloride, 1-Benzyl-3-methylimidazolium chloride, 1,3-dimethylimidazolium chloride, 1,2-dimethyl-3-propylimidazolium chloride, 1-butylpyridinium bromide, 1-butyl-3-methylpyridinium, 1-butyl-3,5-dimethylpyridinium, 1-methyl-3-octylimidazolium bromide, 1-octyl-3-methylimidazolium bromide, 1-ethyl-3-methylimidazolium bromide, 1-hexyl-3-methylpyridinium bromide, 1-butyl-3-methylimidazolium bromide, 1-n-butyl-3-methylimidazolium bromide, 3-hexyl-1-methyl-1H-imidazolium bromide, 1-butyl-4-(dimethylamino)pyridinium bromide, 1-ethyl-2,3-dimethylimidazolium bromide, 4-(dimethylamino)-1-hexylpyridinium, 4-(dimethylamino)-1-hexyl-3-methylpyridinium bromide, 1-hexyl-4-(4-methyl-1-piperidinyl)pyridinium bromide, 1,2,3,4,5-pentamethylimidazolium iodide, 1-ethyl-3-methylimidazolium iodide, 1-butyl-3-methylimidazolium iodide, 1-methyl-3-(1-methylethyl)imidazolium iodide, 1-hexyl-3-methylimidazolium iodide, and combinations thereof.

The term "Hydrophobic Ionic Liquid" refers to an ionic liquid or combination of ionic liquids selected from but not limited to the following: 1,2,3,4,5-pentamethylimidazolium hexafluorophosphate, 1,2-dimethyl-3-propylimidazolium hexafluorophosphate, 1-Butyl-2,3-dimethylimidazolium hexafluorophosphate, 1-Butyl-3-methylimidazolium bis(trifluoromethanesulfonyl)imide, 1-Butyl-3-methylimidazolium hexafluorophosphate, 1-dodecyl-3-methylimidazolium hexafluorophosphate, 1-ethyl-2,3-dimethylimidazolium hexafluorophosphate, 1-ethyl-2,3-dimethylimidazolium hexafluorophosphate [DMEIPF6], 1-Ethyl-3-methylimidazolium bis(trifluoromethanesulfonyl)imide, 1-ethyl-3-methylimidazolium hexafluorophosphate, 1-heptyl-3-methylimidazolium hexafluorophosphate, 1-hexyl-3-methylimidazolium hexafluorophosphate, 1-methyl-3-(1-methylethyl)imidazolium hexafluorophosphate, 1-methyl-3-octylimidazolium hexafluorophosphate, 1-octyl-3-methylimidazolium hexafluorophosphate, 1-methyl-3-pentylimidazolium hexafluorophosphate, 1-pentyl-3-methylimidazolium hexafluorophosphate, 1-methyl-3-propylimidazolium hexafluorophosphate, 1-nonyl-3-methylimidazolium hexafluorophosphate, N,N,N-triethylethanaminium hexafluorophosphate, tetraethylammonium hexafluorophosphate, N-Butyl-3-methylpyridinium hexafluorophosphate, 1-ethyl-3-methylimidazolium (EMI+) perfluoroalkyltrifluoroborates ([RfBF3]-), N-methyl-N-alkylpyrrolidinium perfluoroalkylsulfonyl)imide, as described in Giovanni B. Appetecchi, Silvera Scaccia, Cosimo Tizzani, Fabrizio Alessandrini, and S. Passerini, J. Electrochem. Soc., Volume 153, Issue 9, pp. A1685-A1691 (2006), 1-alkyl-3-methylimidazolium bis(perfluoromethylsulfonyl)imide as described in Brian D. Fitchett, Julie B. Rollins, and John C. Conboy, J. Electrochem. Soc., Volume 152, Issue 8, pp. E251-E258 (2005) and U.S. Pat. No. 5,827,602 issued on Oct. 27, 1998 to Koch, et al, and combinations thereof.

The term "ionic liquid" refers to molten salts comprising anions and cations in a wholly or partially dissociated state such that they exhibit ionic, but not electronic, conductivity. An ionic liquid is a salt that is liquid at temperatures below 100° C. or at room temperature.

The term "noble metal" is accorded its ordinary definition as comprising gold, silver, and the platinum group, namely, platinum, rhodium, palladium, ruthenium, osmium, and iridium, or even the more noble base metals such as copper or nickel.

The term "conducting support substrate" refers to the substrate of a sensor upon which the various layers (i.e., metal, metal salt, ionic liquid, etc.) of the sensor are applied, formed, or deposited.

Thus, there has been described a novel microfabricated liquid junction reference electrode which is sufficiently robust and long lasting. It will be apparent to those skilled in the art from this disclosure, however, that many changes, variations, modifications, other uses, and applications to the microfabricated reference electrode are possible, and also such changes, variations, modifications, other uses, and applications which do not depart from the spirit and scope of the invention are deemed to be covered by the invention, which is limited only by the claims which follow.

What is claimed is:

1. A microfabricated reference electrode comprising an M/MX type reference electrode in contact with a $X^-$ Containing Ionic Liquid having a constant activity of $X^-$, which $X^-$ Containing Ionic Liquid separates the reference electrode from an aqueous analyte, wherein the electrode is further separated from the aqueous analyte by a porous thin-film membrane impregnated with a Hydrophobic Ionic Liquid, wherein the thin-film membrane is comprised of material selected from the group consisting of cellulose, polyethylene oxide, polyethylene glycol gel, or combinations thereof.

2. The reference electrode of claim 1, wherein M is a noble metal and X is a halide.

3. The reference electrode of claim 1, wherein M is selected from the group consisting of silver, gold, platinum, rhodium, palladium, ruthenium, osmium, iridium, copper, nickel, or combinations thereof.

4. The reference electrode of claim 1, wherein X is selected from the group consisting of chloride, bromide, iodide, fluoride, sulfate, phosphate, bicarbonate, hydroxide, or combinations thereof.

5. The reference electrode of claim 1, wherein the electrode is further comprised of a conducting support substrate.

6. The reference electrode of claim 5, wherein the conducting support substrate is isolated from the aqueous analyte by an insulator.

7. The reference electrode of claim 1, wherein M is silver.

8. The reference electrode of claim 1, wherein MX is silver chloride.

9. The reference electrode of claim 1, wherein M/MX is silver/silver chloride.

10. A method for making a microfabricated reference electrode comprising the steps of:
   a) depositing in a non-conducting structure a first layer comprised of a conductive noble metal;
   b) forming an M/MX type reference electrode by treating the first layer with a reagent to produce a second layer comprised of a metal salt, wherein M is a noble metal, and X is a halide;
   c) filling the non-conducting structure with a $X^-$ Containing Ionic Liquid having a constant activity of $X^-$; and
   d) placing a porous thin-film membrane over the $X^-$ Containing Ionic Liquid, the thin-film membrane being comprised of material selected from the group consisting of cellulose, polyethylene oxide, polyethylene glycol gel, or combinations thereof.

11. The method of claim 10, wherein the thin-film membrane is impregnated with a Hydrophobic Ionic Liquid.

12. The method of claim 10, wherein M is selected from the group consisting of silver, gold, platinum, rhodium, palladium, ruthenium, osmium, and iridium, copper, nickel, or combinations thereof.

13. The method of claim 10, wherein X is selected from the group consisting of chloride, iodide, fluoride, bromide, sulfate, phosphate, bicarbonate, hydroxide, or combinations thereof.

14. The method of claim 10, further comprising the step of contacting the first layer to a conducting support substrate.

15. The method of claim 10, wherein the conducting support substrate is isolated from the aqueous analyte by an insulator.

16. The method of claim 15, wherein the conducting support substrate comprises an electrically conducting material.

17. The method of claim 16, wherein the electrically conducting material is selected from the group consisting of aluminum, noble metals, or combinations thereof.

18. The method of claim 10, wherein M is silver.

19. The method of claim 10, wherein MX is silver chloride.

20. The method of claim 10, wherein M/MX is silver/silver chloride.

* * * * *